United States Patent
Haughton

(10) Patent No.: US 11,311,703 B2
(45) Date of Patent: *Apr. 26, 2022

(54) CEREBROSPINAL FLUID FLOW DIVERTER

(71) Applicant: Victor M. Haughton, Oconomowoc, WI (US)

(72) Inventor: Victor M. Haughton, Oconomowoc, WI (US)

(*) Notice: Subject to any disclaimer, the term of this patent is extended or adjusted under 35 U.S.C. 154(b) by 591 days.

This patent is subject to a terminal disclaimer.

(21) Appl. No.: 16/266,087

(22) Filed: Feb. 3, 2019

(65) Prior Publication Data

US 2019/0167957 A1 Jun. 6, 2019

Related U.S. Application Data

(63) Continuation of application No. 15/176,705, filed on Jun. 8, 2016, now Pat. No. 10,207,089.

(Continued)

(51) Int. Cl.
*A61M 27/00* (2006.01)
*A61M 25/10* (2013.01)
*A61M 39/06* (2006.01)

(52) U.S. Cl.
CPC .... *A61M 27/006* (2013.01); *A61M 25/10185* (2013.11); *A61M 39/06* (2013.01); *A61M 25/10183* (2013.11); *A61M 2039/062* (2013.01); *A61M 2210/0687* (2013.01); *A61M 2210/0693* (2013.01); *A61M 2230/005* (2013.01); *A61M 2230/30* (2013.01)

(58) Field of Classification Search
CPC .... A61M 2039/062; A61M 2210/0687; A61M 2230/30; A61M 27/006; A61M 25/10183
See application file for complete search history.

(56) References Cited

U.S. PATENT DOCUMENTS 3,233,610 A  2/1966 Wade
3,583,387 A * 6/1971 Garner ............... A61M 27/006
                                                      600/561

(Continued)

FOREIGN PATENT DOCUMENTS

DE    8811322.1 U1   12/1988
FR    2274261 A1      9/1976

OTHER PUBLICATIONS

J Neurosurg. Nov. 2004;101(2 Suppl):169-78. Foramen magnum cerebrospinal fluid flow characteristics in children with Chiari I malformation before and after craniocervical decompression. Iskandar BJ, Quigley M, Haughton VM.

(Continued)

*Primary Examiner* — Leslie R Deak
(74) *Attorney, Agent, or Firm* — Koffsky Schwalb LLC; Mark I. Koffsky

(57) ABSTRACT

A device that can be placed within or near the cranial vault that fluctuates in size in response to changes in CSF pressure is disclosed. The device diminishes in size when CSF pressures rise and increases in size as CSF pressures diminish. The device has the effect of reducing the flow of CSF occurring in the foramen magnum and provides an alternative to craniovertebral decompression in Chiari I patients. The device may have applications in other neurologic illnesses associated with abnormal CSF flow, such as Idiopathic Syringomyelia, Normal Pressure Hydrocephalus, and CSF dural leaks.

11 Claims, 7 Drawing Sheets

Related U.S. Application Data

(60) Provisional application No. 62/173,820, filed on Jun. 10, 2015.

(56) References Cited

U.S. PATENT DOCUMENTS

| | | | |
|---|---|---|---|
| 4,026,276 | A | 5/1977 | Chubbuck |
| 4,127,110 | A | 11/1978 | Bullara |
| 4,769,002 | A | 9/1988 | Hooven |
| 4,781,672 | A | 11/1988 | Hooven |
| 5,683,357 | A | 11/1997 | Magram |
| 5,873,840 | A | 2/1999 | Neff |
| 6,533,733 | B1 | 3/2003 | Ericson et al. |
| 7,189,221 | B2 | 3/2007 | Silverberg et al. |
| 7,309,330 | B2 | 12/2007 | Bertrand et al. |
| 7,513,883 | B2 | 4/2009 | Glenn |
| 8,956,379 | B2 * | 2/2015 | Luciano .............. A61M 60/135 606/192 |
| 2006/0020239 | A1 | 1/2006 | Geiger et al. |
| 2011/0160609 | A1 | 6/2011 | Stone |
| 2012/0172751 | A1 | 7/2012 | Levin |
| 2015/0005800 | A1 | 1/2015 | Anile |

OTHER PUBLICATIONS

AJNR Am J Neuroradiol. Jan. 2004;25(1):142-5. Effect of craniocervical decompression on peak CSF velocities in symptomatic patients with Chiari I malformation. Dolar MT, Haughton VM, Iskandar BJ, Quigley M.

AJNR Am J Neuroradiol. Jan. 2013;34(1):41-5. doi: 10.3174/ajnr. A3282. Epub Aug. 16, 2012. Simulating CSF flow dynamics in the normal and the Chiari I subarachnoid space during rest and exertion. Linge SO, Mardal KA, Haughton V, Helgeland A.

AJNR Am J Neuroradiol. Sep. 2011;32(8):1474-81. doi: 10.3174/ajnr.A2496. Epub May 19, 2011. Effect of tonsillar herniation on cyclic CSF flow studied with computational flow analysis. Linge SO, Haughton V, Lovgren AE, Mardal KA, Helgeland A, Langtangen HP.

Chiari Malformation:Treatment, C&S Patient Education Foundation, 2012.

ISR and Written Opinion of ISA/US in PCT/US2016/36458 (dated Oct. 14, 2016).

Communication from EPO for Application No. 16808195.8, dated Apr. 24, 2020.

Extended European search report for Application No. 16808195.8, dated Mar. 6, 2019.

\* cited by examiner

CEREBROSPINAL FLUID FLOW DIVERTER

RELATED APPLICATION

This application claims the benefit of U.S. Provisional Patent Application Ser. No. 62/173,820 filed on Jun. 10, 2015.

FIELD OF THE DISCLOSURE

The present invention relates to the field of neurosurgical devices and procedures, and in particular, devices and procedures for alleviating neurological disorders associated with cerebrospinal fluid (CSF) flow.

BACKGROUND

Since the normal human skull is rigid, transient volume variations in intracranial structures, such as cerebral vasculature and brain, cause the intracranial cerebrospinal fluid (CSF) to flow from the cranial vault into the spinal canal. (Mokri 2001). As a result, CSF flows cyclically through the foramen magnum, which connects the cranial vault and the spinal canal.

About 0.7% of the U.S. population suffers from a congenital disorder known as the Chiari I malformation, wherein the cerebellar tonsils are located in the upper cervical spinal canal. In Chiari I patients, the displacement of fluid from the cranial vault is partially obstructed at the level of the foramen magnum, with the result that CSF velocities and pressures in the foramen magnum increase. (Linge 2011). A fraction of Chiari I patients develop complications such headache, or syringomyelia (spinal cord cyst) and motor and sensory deficits.

Craniovertebral decompression is the standard surgical treatment for suitable Chiari I cases and generally Chiari I with syringomyelia. This procedure typically consists of enlarging the foramen magnum and upper cervical spinal canal so as to facilitate the flow of CSF and reduce fluid velocities and pressure gradients. (Linge 2014) In the U.S., surgeons have performed over 10,000 such decompressions annually since 2007 (reference: Labuda, "Chiari Malformation: Treatment," C&S Patient Edu. Found., 2012). The Academy of Neurologic Surgeons reports 14, 131 cases of "Chiari decompression (CPT codes 61343, 61345) in 2011. The procedure in most patients reduces or eliminates the syringomyelia within a few months. Craniovertebral decompression is usually safe and effective but, in one report, one third of patients had complications including vertebral artery injury, spinal cord injury, nerve root injury, suffocation, cerebrospinal fluid leakage, and infection (Barong 2014).

Bermans Iskandar (Iskandar 2004) and Maria Dolar (Dolar 2004) have shown that craniovertebral decompression decreases CSF velocities in the foramen magnum. In theory, the craniovertebral decompression improves CSF flow to alleviate symptoms. But there remain different theories on the mechanism(s) by which decompression achieves therapeutic results.

Other less frequently-used surgical procedures for treating Chiari I patients include CSF shunting, de-tethering of the spinal cord, and marsupialization of spinal cord cysts, generally with complications and/or a lower rate of therapeutic success than decompression. In conventional treatments for this disorder, inserting a catheter is not a highly effective method of treatment and is not based on a well-designed scientific model. Instead, the protocol is simply to remove fluid rather than correct the underlying physiologic abnormality. But the real problem in this condition is the increased amplitude of the cyclic pressure wave.

In contrast, the disclosed invention consists of an implantable, biocompatible, and Magnetic Resonance (MR) compatible device (where non MR compatible elements may be readily removed before any MR testing). The disclosed invention functions as a chamber that effectively varies in size as CSF pressure changes, decreasing as CSF pressure increases and increasing as CSF pressure decreases, by utilizing passive compliant as well as active compliant members to modulated CSF pressure fluctuations and to modify related CSF flow. Placed within the CSF fluid spaces of the cranial vault, the disclosed device, in various embodiments, effectively, diverts spinal fluid flow from the foramen magnum and damps cyclic CSF pressure pulsations related to the cardiac cycle. This diversion of flow diminishes cyclic CSF fluid flow in the foramen magnum, which is theoretically the cause of spinal cord cysts in Chiari patients. Including instrumentation to measure the pressure values over time may also provide diagnostic information and measure of the condition. The instrumentation also monitors the function of the device, monitors intracranial pressure fluctuations and determines the need for a changing the volume of the chamber in the device.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Figure 1:
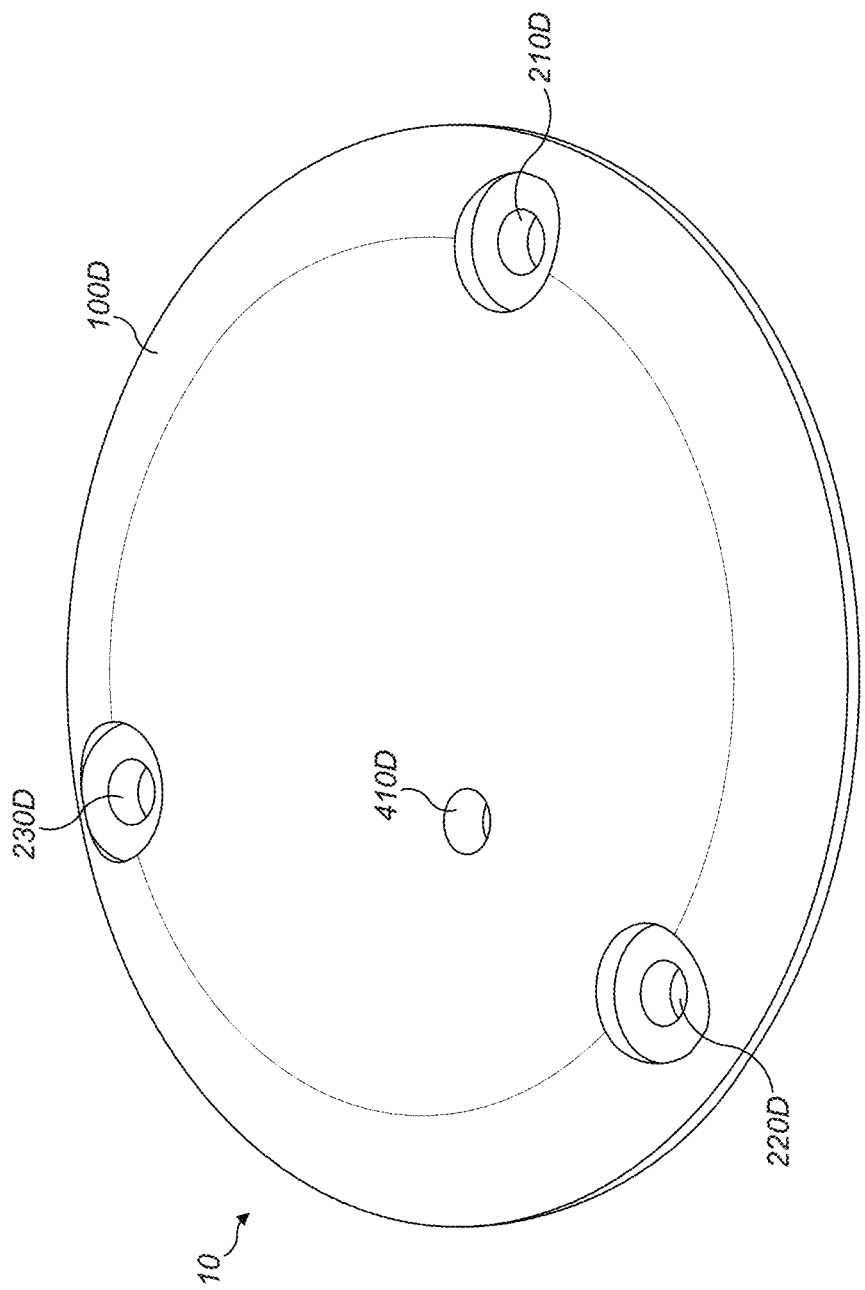
FIG. 1 is a top view of a fully-assembled CST diverter device in accordance with some embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

I. Introduction

The CSF flow diverter contains a structure that effectively contracts when the CSF pressure rises and expands when CSF pressure decreases. It is essentially a chamber with the property of changing in volume as intracranial pressure changes the device may be a passive system comprised of a flexible membrane or flexible membranes that covers the chamber, providing a standard compliance greater than normal cranial compliance (change in volume for change in pressure). Or the device may have an experimentally-determined compliance charged with a known or experimentally-determined value that serves to provide the compliance required to address the adverse CSF pressures associated with the blockage of the normal CSF channels or abnormal compliance in the cranial vault. Alternatively, the device may consist of actively controlled elements that are controlled by either dynamic or static measurements of the existing CSF pressure values and actively adjusted, at near real time, or a nominal control value to alleviate the adverse CSF pressure values. Alternatively, the device may also consist of a compressible material such as foam rubber or a flexible chamber that contains springs.

The CSF flow diverter is intended for implantation in a craniotomy defect and fastening to the skull so as to provide a rigid outer surface and a non-rigid inner surface. Alternatively, the elastic structure in the chamber may be placed in the cranial vault near the craniotomy. The elastic structure may be replaced by a gas filled balloon, which is attached to a catheter so that the balloon may be introduced into a ventricle, as in a typical ventricular cannulation. The balloon changes in volume with changes in intracranial pressure. The amount of pressure and of gas in the balloon may be changed by moving air through the attached catheter into the balloon. A small reservoir on the surface of the skull under the scalp enables the introduction or removal of air with a syringe and needle inserted through a nib into the reservoir. This embodiment of the device has applications when the ventricles are sufficiently enlarged to permit the placement of the balloon. Patients with Normal Pressure Hydrocephalus are one such patient group.

The CSF flow diverter may be a vehicle for the placement of tissue or compressible fluid beneath a craniotomy flap in such a way as to alter the effective compliance of the cranial vault. Thus, the CSF flow diverter serves is an implantable device placed below a craniotomy flap in such a way as to alter the effective compliance of the cranial vault. The device incorporates a chamber or a conduit configured to create a small reservoir to create a larger intracranial volume reversibly as needed to modulate changes in CSF pressure.

Further, the CSF flow diverter may act as an implantable device that is configured to be attached to a spinal column in such a way as to modify the spinal column's effective compliance. The device may further include a monitor that allows external non-invasive monitoring of the device's functioning. The device may further comprise a controller that permits selectable increase or decrease of the device's compliance in either near real time, at a fixed relationship or at real time.

II. Nomenclature

In these foregoing descriptions, each subpart of the CSF flow diverter shown in FIGS. 1-5 has the same numerical reference and may optionally also be referenced with a letter suffix that varies depending on which figure is being discussed. For example, the cover level 100 is shown from various angles in FIG. 1 (assembled top view 100D), FIG. 2 (assembled bottom view 100E), FIG. 3 (exploded top view 100A), FIG. 4 (exploded bottom view 100B) and FIG. 5 (section view) 100C). Thus, all of these views of the cover level 100A, 100B, 100C, 100D, 100E represent the same cover level 100.

III. Review of the Drawings

Turning to FIG. 1, shown is a top view 10 of a fully-assembled CSF flow diverter. Shown is a top portion of a cover level 100D which includes the top portion of a multitude of holes 210D, 220D, 230D. The plurality of holes 210D, 220D, 230D are designed to be secured to the cranium via securing mechanisms such as medical screws (not shown). Also shown is the top portion of a nib 410D that is drilled all the way through the cover level 100D so as to allow limited access to levels below the cover level 100D.

Figure 2:
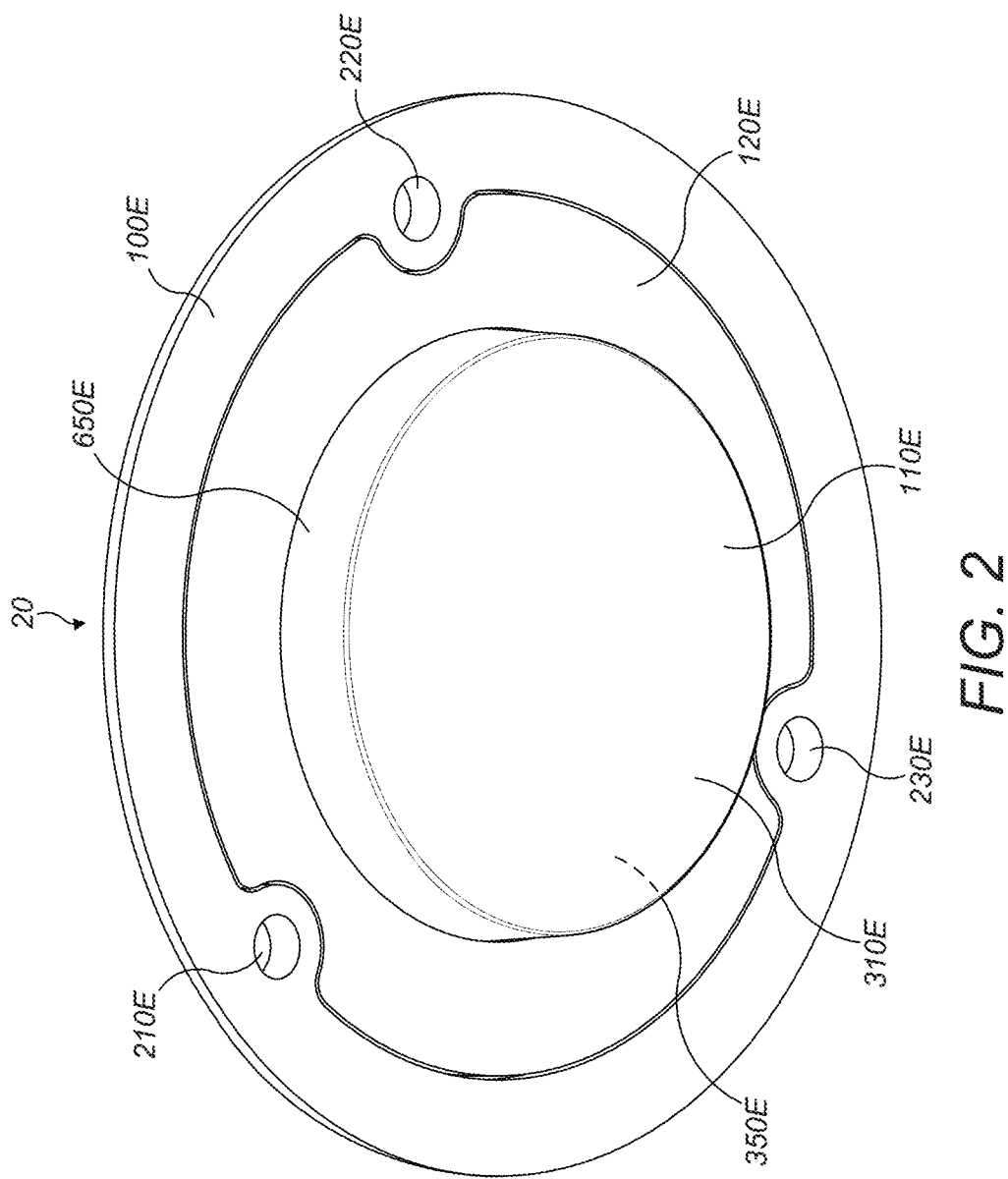
FIG. 2 is a bottom view of a fully-assembled. CSF diverter in an accordance with some embodiments.

Turning to FIG. 2, shown is a bottom view 20 of a fully-assembled CSF flow diverter. Shown is the bottom portion of a cover level 100E which includes the bottom portion of a multitude of holes 210E, 220E, 230E. Also shown is the bottom portion of a membrane level 110E. This level consists of the bottom portion of the flexible membrane 310E that incorporates a chamber 350E above. The membrane level incorporates a side portion 650E that is tapered so as to provide the proper interference fit to a cranium of a patient.

Figure 3:
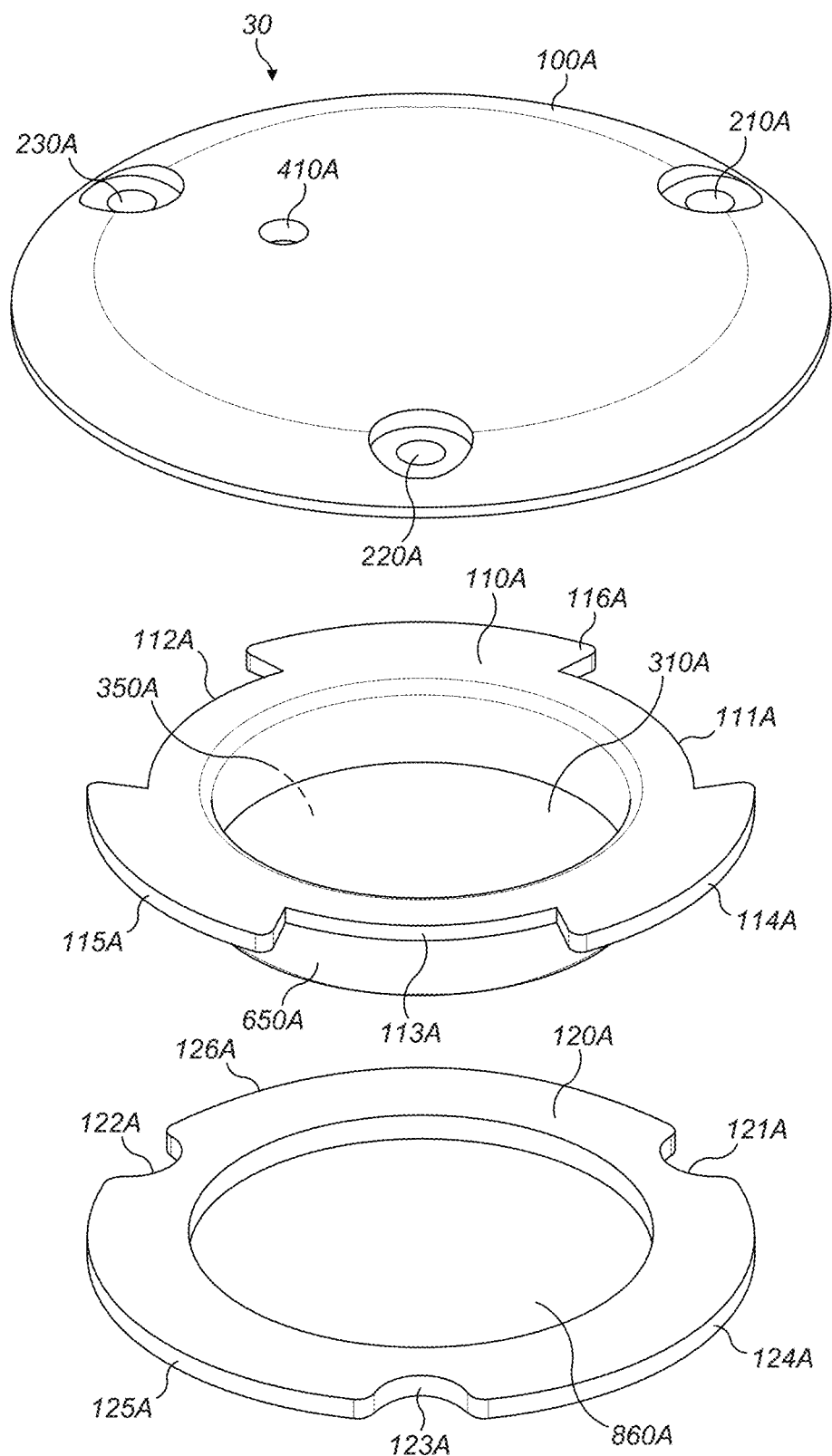
FIG. 3 is an exploded top view of a CSF diverter in accordance with some embodiments.

Turning to FIG. 3, shown is an exploded top view 30 showing the three levels of the CSF flow diverter: the cover level 100A, the membrane level 1101 and the retaining level 120A.

The cover level 100A shown includes the top portion of a plurality of holes 210A, 220A, 230A. Also shown is the top portion of a nib 410A that is drilled all the way through the cover level 100A so as to allow limited access to levels below the cover level 100A. The cover level 100A may consist of polyether ether ketone (PEEK) as well with a hydroxyapatite coating for bone adhesion. PEEK is a colorless organic thermoplastic polymer in the polyaryletherketone (PAEK) family. PEEK is an advanced biomaterial used in medical implants, including spinal fusion devices, reinforcing rods and other orthopedic procedures.

The membrane level 110A incorporates a flexible membrane 310A which forms the bottom boundary of the chamber 350A (the top boundary being the cover level 100A). The membrane level 110A incorporates a side portion 650A that is tapered so as to provide the proper interference fit to a cranium of a patient. The top portion of the membrane level incorporates a plurality of sawtooth members 114A, 115A, 116A interspersed with a plurality of large cutouts 111A, 112A, 113A.

The retaining level 120A incorporates a plurality of retaining members 124A, 125A, 126A interspersed with small cutouts 121A, 122A, 123A. The retaining level 120A is designed to secure the membrane level 110A to the cover level 100A so that the membrane level 120A is sandwiched in between. When so assembled, the small cutouts 121A, 122A, 123A allow access for the securing mechanisms (not shown) to pass through the plurality of holes 210A, 220A, 230A and into the cranium of the patient. Further the side portion 650A and the flexible membrane 310A pass through the hole 860A when so assembled.

Figure 4:
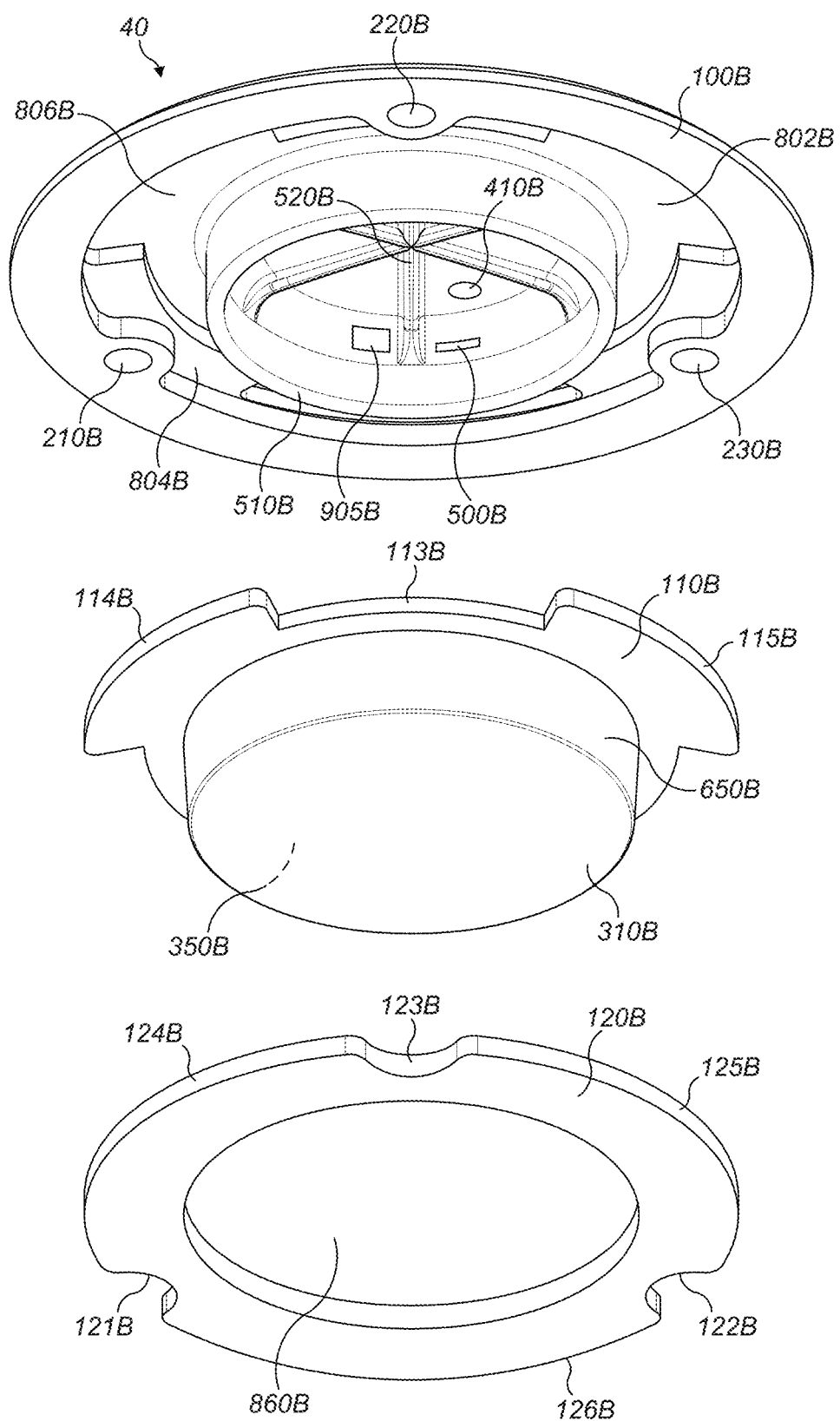
FIG. 4 is an exploded bottom view of a CSF diverter in accordance with some embodiments.

Turning to FIG. 4, shown is an exploded bottom view 40 showing the three levels of the CSF flow diverter: the cover level 100B, the membrane level 110B and the retaining level 120B. The cover level 100B shown includes the bottom portion of a plurality of holes 210B, 220B, 230B. Also shown is the bottom portion of a nib 410B that is drilled all the way through the cover level 100B. This view also shows the underside of the cover level 100B, showing a plurality of struts 520B providing structural support for the CSF flow diverter. Also shown is a stopper 500B attached to the struts 520B that is situated below the nib 410B. Also shown are a plurality of tooth holders 802B, 804B, 806B that serve as a receptacle for portions of the membrane level 110B as discussed below. Also shown is a monitoring/control mechanism 905B that may be attached to the struts 520B and allow for the monitoring and/or control of the operation of the CSF flow diverter.

The membrane level 110B incorporates a flexible membrane 310B which forms the bottom boundary of the chamber 350B (the top boundary being the cover level 100B). The membrane level 110B incorporates a side portion 650B that is tapered so as to provide the proper interference fit to a cranium of a patient. The top portion of the membrane level incorporates a plurality of sawtooth members 114B, 115B, 116B (116B is not shown) interspersed with a plurality of large cutouts 11B, 112B, 113B (111B, 112B are not shown). The sawtooth members 114B, 115B, 116B are designed to be bonded with the tooth holders 802B, 804B, 806B, thus securing the cover level 100B to the membrane level 110B.

The retaining level 120B is ring-shaped with a hole 860B that incorporates a plurality of retaining members 124B, 125B, 126B interspersed with small cutouts 121B, 122B, 123B. The retaining level 120B is designed to be bonded with the cover level 100B with the membrane level sandwiched in between. When so assembled, the small cutouts 121B, 122B. 123B allow access for the securing mechanisms (not shown) to pass through the plurality of holes 210B, 220B, 230B and into the cranium of the patient. Further the side portion 650B and the flexible membrane 310B pass through the hole 860B when so assembled.

Figure 5:
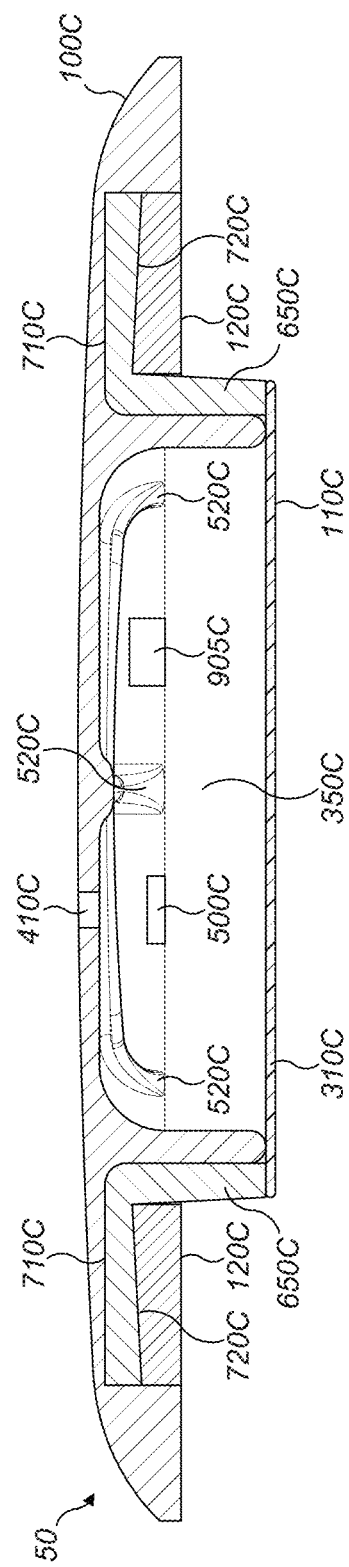
FIG. 5 is a front sectional view of a CSF diverter in accordance with some embodiments.

Turning to FIG. 5, shown is a front section view 50 of a fully-assembled CSF flow diverter. From this view, the interfacing of the cover level 100C, membrane level 110C and retaining level 120C among each other is readily observable. In particular, the bonded areas 710C, 720C show how the retaining level 120C is used to secure the membrane level 110C to the cover level 100C. Also shown is a cutaway of the struts 520C, the nib 410C, the stopper 500C, the chamber 350C, the flexible membrane 310C, the side portion 650C and the monitoring/control mechanism 905C.

IV. Physical Features of CSF Flow Diverter

The cover level 100 may be made from polyether ether ketone (PEEK) as well with a hydroxyapatite coating for bone adhesion. PEEK is a colorless organic thermoplastic polymer in the polyaryletherketone (PAEK) family. PEEK is an advanced biomaterial used in medical implants, including spinal fusion devices, reinforcing rods and other orthopedic procedures. The cover level 100 may also be comprised of plastics, or titanium or other metals that may be compatible with MRIs and transparent to ultrasound. The nib 410 may be made from a rubber-like material through which a needle can be advanced with a rigid part to hold the rubber in place and a guard to prevent the needle from entering the chamber 350 too deeply.

The membrane level 110 may also be made from PEEK, plastics, or titanium or other metals that may be compatible with MRIs and transparent to ultrasound, except that the flexible membrane 310 may be fabricated from materials such as ultra-high-molecular-weight polyethylene (UHMW PE) or the like compliant bio-compatible materials provides the compliance described herein. UHMWPE has a long history as a successful biomaterial for use in hip, knee, and spine implants. The flexible membrane 310 may also be comprised of a flexible metal alloy diaphragm.

The retaining level 120 may be made from PEEK, plastics, or titanium or other metals that may be compatible with IOUs and transparent to ultrasound.

V. Operation of CSF Flow Diverter

As an implantable device, the CSF flow diverter is configured to reversibly increase the capacity of the cranial vault in response to a pressure change in the CSF. The CSF flow diverter is designed for placement in a craniotomy, or, in lay terms, a hole created surgically in the skull. A CSF flow diverter placed in the skull decreases CSF pressure gradients and thus reduces CSF flow through the foramen magnum, and reduces CSF velocities in the cervical spine. The CSF flow diverter may be located in a position may be placed in the craniotomy defect in place of a bone flap. Alternatively, the elastic chamber or cushion or materials in the chamber may be placed in the cranial vault. The device contains biocompatible materials where it is in contact with the human body.

The CSF flow diverter may be made in variable sizes and configurations between 11 mm and 18 mm in diameter for example, or more particularly, 16.5 mm in diameter.

The chamber 350 includes a compressible material located therein and the volume of the chamber 350 is selectively increased or decreased in volume by the ongoing displacement of the flexible membrane 310, thereby providing the desired clinical relief by diverting the CSF flow.

The volume in the chamber a 350 may be modified by intervention from the treating physicians. For example, a surgeon or physician may administer or remove gas (e.g. nitrogen or oxygen) through the nib 410 into the chamber 350 to achieve suitable pressure to increase or decrease the overall diversion of the CSF flow. The stopper 500 is situated below the nib 410 so as to prevent the needle piercing the nib 410 from going beyond the stopper 500 and puncturing or damaging the flexible membrane 310.

The chamber 350 may be filled with compressible gas such as oxygen or nitrogen (administered via the nib 410). Other possibilities for inclusion in the chamber include: 1) a compressible tissue such as foam rubber or a compressible mechanism such as a chamber fitted with springs; 2) utilizing an electric or bio-powered control element such as a pump or "Shape Memory Alloy" wherein the shape is proportional to a controlled temperature that may be altered electronically by utilizing heating or cooling systems as well as the natural surrounding temperatures.

The size of the chamber 350, may be designed to be directly proportional to the effect on CSF flow. For example, a circular chamber with a 1 cm diameter that moves 3 mm between systole and diastole would reduce Foramen Magnum flow in the average adult from 2 mL to 1 mL. Such movements would modify the CSF pressure to reduce CSF flow and reduce CSF velocities in the spine and improve patient comfort and reverse the growth of syringomyelia. Putting this another way, the chamber 350 may vary in volume by an exemplary 1 to 2 mL during the cardiac cycle, which serves to reduce the amount of fluid displaced from the cranial vault through the Foramen Magnum by any adjustable amount, such as from 50 to 100%.

The chamber 350 may also include a monitoring/control mechanism 905, which may include a battery, sensors, transmitters and assorted housings. The monitoring/control mechanism 905 may include additional electronic elements designed to provide either near real time or a fixed pressure delivery protocol utilizing pressure sensors, strain gages, or the like designed to monitor and/or alter the operation of the chamber 350 and the flexible membrane 310. There may be elements that can be remotely programmed to provide the level of compliance based on the near real time measurement of the CSF pressures or on signals that encode membrane movement or intracranial volume. With this system the patient can be assured of proper CSF pressure and flow control to provide better outcomes. Well known wireless communication protocols not requiring the attachment of wires to the device may allow the surgeon to provide the necessary adjustments based on other external measurements and tests to provide a swift adjustment for the patient.

VI. Intraventricular Balloon Catheter

Figure 6:
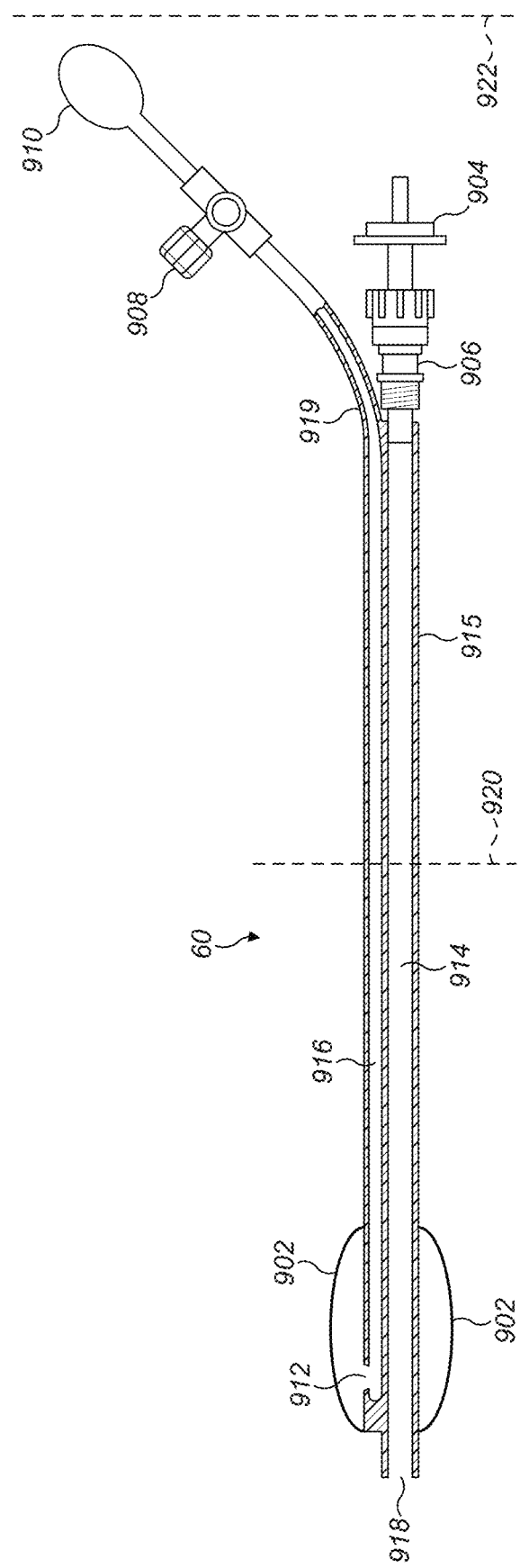
FIG. 6 is a side sectional view of a second version of a CSF diverter in accordance with some embodiments.

As a second embodiment, CSF pressure may be modulated by the implantation and operation of an intraventricular balloon catheter. Shown in FIG. 6 is a side sectional view of an intraventricular balloon catheter 60 incorporating a balloon lumen 916 and a trochar lumen 914 surrounded by a tube jacket 915. The tube jacket may comprise carbothane. The distal end of the balloon lumen 916 includes a balloon aperture 912 that is connected to the balloon 902. The balloon 902 surrounds all sides of the distal end of the tube jacket 915. The balloon may comprise urethane. The distal end of the trochar lumen 914 incorporates a trochar aperture 918, which is designed to be inserted into a lateral ventricular space within a patient. The trochar 904 itself may be selectively inserted and removed by the physician from the trochar lumen 914 to provide stiffness within the tube jacket 915.

On the proximal end of the trochar lumen 914 is a hemostasis valve 906 that can be sealed upon the withdrawal of the trochar 904 from the trochar lumen 914. The hemostasis valve 906 may also be accessed to allow CSF to be removed via a drainage catheter (not shown).

On the proximal end of the balloon lumen 916 is a dual port hub 908 and a balloon reservoir 910. The dual port hub 908 is capable of interfacing with a gas supply (not shown) to either add or withdraw gas from the chambers that are holding the gas, which include the balloon 902, the balloon lumen 916 and the balloon reservoir 910. The gas may comprise sterile air, nitrogen or other appropriate gases.

Figure 7:
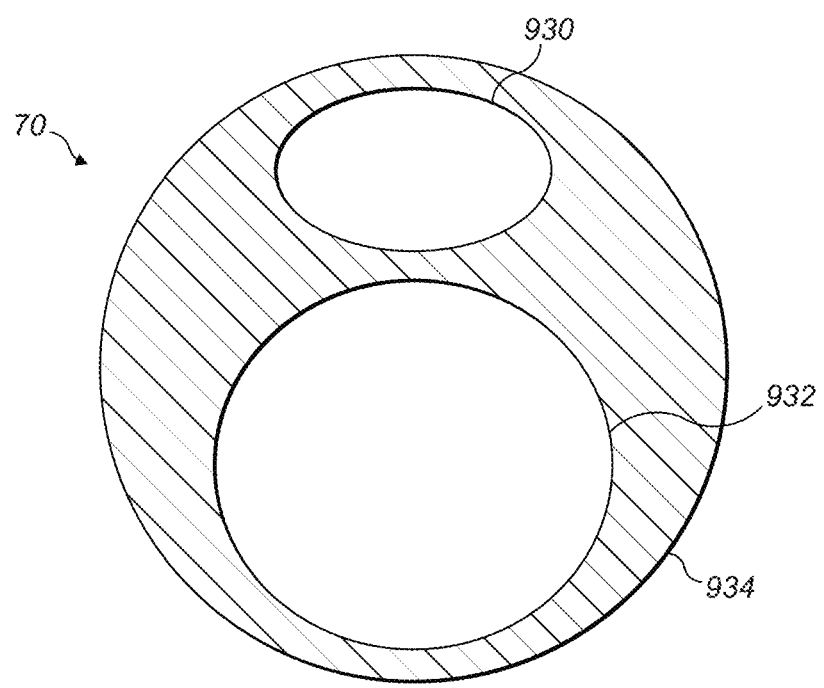
FIG. 7 is a front sectional view of a second version of a CSF diverter in accordance with some embodiments.

Turning to FIG. 7, shown is a front sectional view of intraventricular balloon catheter 60 taken at the skull 920. Shown is a tube jacket cutaway 934 surrounding the balloon lumen cutaway 930 and the trochar lumen cutaway 932. As can be seen, the diameter of the balloon lumen cutaway 930 is smaller than the trochar lumen cutaway 932 because the balloon lumen 916 contains gas, which is less viscous. The trochar lumen 932 contains CSF and thus needs to be larger because the fluid is more viscous. The diameter of the balloon lumen cutaway 930 may be 0.020 inches; the diameter of the trochar lumen cutaway 9:32 may be 0.032 inches; the diameter of the tube jacket cutaway may be 0.078 inches.

Insertion of the intraventricular balloon catheter 60 in the patient may proceed as follows. The physician makes appropriate incisions in the scalp 922 and the skull 920 of the patient. With the trochar 904 inserted into the trochar lumen 914 (to provide stiffness), and the balloon 902 deflated, the distal end of the intraventricular balloon catheter 60 is inserted through the scalp 922 and the skull 920 so that the trochar aperture 918 is inserted into a lateral ventricular space within a patient. The trochar 904 is removed from the trochar lumen 914 and the hemostasis valve 906 is sealed to prevent leakage of CSF. An appropriate amount of gas is inserted through the dual port hub into the balloon 902, the balloon lumen 916 and the balloon reservoir 910. This has the effect of inflating the balloon 902.

After these steps are taken, a bend 919 is used to allow the proximal portion of the intraventricular balloon catheter 60 to be bent and tucked in between the scalp 922 and the skull 920. The scalp 922 is then repaired. The advantage of this placement is that if adjustment to the gas is necessary, the physician may adjust the gas by way of the dual port hub 908 by reopening the scalp 922 without needing to further access the skull 920 of the patient. Similarly, if adjustment to CSF is necessary, the physician may adjust the CSF by way of the hemostasis valve 906 without needing to further access the skull 920 of the patient.

Once the intraventricular balloon catheter 60 is installed in the patient, increasing CSF pressure during the cardiac cycle causes the balloon 902 to diminish in size. At the same time, the gas is forced through the balloon aperture 912 and then through the balloon catheter 916 and into the balloon reservoir 910. Conversely, decreasing CSF pressure during the cardiac cycle causes the balloon 904 to increase in size because the gas flows back from the balloon reservoir 910, through the balloon catheter 916 and into the balloon 902 through the balloon aperture 912. This effectively change the compliance of the skull from poorly compliant to finitely more compliant such that the intracranial pressure changes less during the cardiac cycle and in particular increases less during systole. The effect of the intraventricular balloon catheter 60 is to reduce the amount of fluid forced from the cranial vault into the upper cervical spinal canal during systole. The intraventricular balloon catheter 60 reduces spinal fluid movement, CSF velocities, CSF pressure gradients and CSF pressure wave magnitudes in the Foramen Magnum.

VII. Other Applications

Another embodiment may be a chamber to place in a craniotomy site over which a rigid plate, for example a metal plate, is placed. Another embodiment is a smaller, simpler device for veterinary use in for example Cavalier King Charles Spaniels that frequently have tonsil malformations and sytingomyelia and symptoms such as weakness in the limbs.

Another embodiment may be a chamber placed outside the skull that has a sufficiently large channel communicating with the intracranial chamber such that changes in CSF pressure cause fluid or gas or tissue to move reversibly between the external chamber and the intracranial chamber. It improves compliance of the cranial vault, modulates CSF pressures and damps CSF pressure waves such as pressure waves occurring in association with the cardiac cycle.

The described inventive matter may also have applications in other disorders. Applications are anticipated in a less frequent condition; Idiopathic Syringomyelia, which is syringomyelia without a Chiari I malformation. It may have applications in Normal Pressure Hydrocephalus, a condition that has abnormal CSF pressure waves, which are often the object of surgical treatment with shunting (Bradley 2000). Since Normal Pressure Hydrocephalus is characterized by abnormally low cranial compliance, use of the device in these patients may be effective. The device may provide more effective control of CSF pressures than conventional shunting in patients with some types of transient CSF pressure fluctuations due, for example, to coughing or sneezing. In patients with CSF leaks from the subarachnoid space, the use of the device will serve to decrease the fluctuations in CSF pressure due to the cardiac cycle, possibly reducing CSF leakage and aiding in the healing of the traumatic dural defects. The described matter seeks to improve compliance, modulate CSF pressures and damp CSF pressure waves such as those occurring with the cardiac cycle.

VIII. Conclusion

It is contemplated that any optional feature of the inventive variations described may be set forth and claimed independently, or in combination with any one or more of the features described herein. Reference to a singular item, includes the possibility that there is a plurality of the same items present. More specifically, as used herein and in the appended claims, the singular forms "a," "an," "said," and "the" include plural referents unless specifically stated otherwise. In other words, use of the articles allow for "at least one" of the subject item in the description above as well as the to be appended claims. It is further noted that the appended claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in the to be appended claims shall allow for the inclusion of any additional element irrespective of whether a given number of elements are enumerated in the to be appended claim, or the addition of a feature could be regarded as transforming the nature of an element set forth in the to be appended claims. Except as specifically defined herein, all technical and scientific terms used herein are to be given as broad a commonly understood meaning as possible while maintaining to be appended claim validity.

The breadth of the present invention is not to be limited to the examples provided and/or the subject specification, but rather only by the scope of the to be appended claim language. Use of the term "invention" herein is not intended to limit the scope of the appended claims in any manner. Rather it should be recognized that the "invention" includes the many variations explicitly or implicitly described herein, including those variations that would be obvious to one of ordinary skill in the art upon reading the present specification. Further, it is not intended that any section of this specification (e.g., the Summary, Detailed Description, Abstract, Field of the Invention, etc.) be accorded special significance in describing the invention relative to another or the to be appended claims. All references cited are incorporated by reference in their entirety. Although the foregoing invention has been described in detail for purposes of clarity of understanding, it is contemplated that certain modifications may be practiced within the scope of the to be appended claims.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

I claim:

1. A cerebrospinal fluid flow diverter, comprising:
   a cover level having a cover top side and a cover underside, the cover level comprising a cap-like structure having a plurality of securing holes from the cover top side through the cover underside;
   a membrane level comprising a plurality of membrane level securing members, a flexible membrane, a tapered side portion, and a component, wherein the flexible membrane forms the bottom boundary of the component and covers it;
   a retaining level comprising a ring-like structure having a substantially circular retaining member with a hollow center;
   a plurality of skull-securing mechanism passing through the plurality of securing holes and into the skull of the patient;
   a nib passing through the cover top side, through the cover underside and opening into the component;

wherein the membrane level is attached to the cover underside by securing the plurality of membrane level securing members between the substantially circular retaining member and the cover underside so that the flexible membrane, the tapered side portion, and the component pass through the hollow center of the substantially circular retaining member and the top of the component is covered by the cover underside;

wherein the component is filled with compressible matter;

wherein after the tapered side portion and the flexible membrane are inserted in a skull of a patient, the volume of the component is selectively increased and decreased in volume by the ongoing displacement of the flexible membrane during a cardiac cycle in the patient, thereby modulating the cerebrospinal flow in the patient.

2. The cerebrospinal fluid flow diverter as in claim 1, further comprising a stopper installed in the component in proximity to the end of the nib opening in the component to prevent damage to the flexible membrane.

3. The cerebrospinal fluid flow diverter as in claim 2, wherein the compressible matter is gas.

4. The cerebrospinal fluid flow diverter as in claim 3, wherein the pressure of the gas is capable of being adjusted by the insertion and removal of the gas via the nib.

5. The cerebrospinal fluid flow diverter as in claim 4, wherein the diameter of the cerebrospinal fluid flow diverter is between 11 mm and 18 mm.

6. The cerebrospinal fluid flow diverter as in claim 4, wherein the volume of the component varies between 1 mL and 2 mL during a cardiac cycle of the patient.

7. The cerebrospinal fluid flow diverter as in claim 1, further comprising a control sensor in the component for managing and controlling the status of the compressible matter and the flexible membrane.

8. The cerebrospinal fluid flow diverter as in claim 7, wherein the control sensor communicates via wireless communication protocols.

9. The cerebrospinal fluid flow diverter as in claim 1, wherein the flexible membrane comprises bio-compatible ultra-high-molecular-weight polyethylene.

10. The cerebrospinal fluid flow diverter as in claim 1, wherein the cover level comprises bio-compatible polyether ether ketone.

11. The cerebrospinal fluid flow diverter as in claim 1, wherein the compressible matter is a compressible tissue.

* * * * *